United States Patent [19]

Nahum

[11] Patent Number: 4,843,186

[45] Date of Patent: Jun. 27, 1989

[54] LONG SHELF LIFE HETEROZYGOUS TOMATO PLANT

[75] Inventor: Kedar Nahum, Rehovot, Israel

[73] Assignee: LSL, Inc., Tiburon, Calif.

[21] Appl. No.: 889,915

[22] Filed: Jul. 28, 1986

[51] Int. Cl.⁴ .............................................. A01H 1/02
[52] U.S. Cl. .......................................... 800/1; 47/58;
47/DIG. 1
[58] Field of Search ................................ 800/1; 47/58

Primary Examiner—Robert E. Bagwill
Attorney, Agent, or Firm—Browdy and Neimark

[57] ABSTRACT

A heterozygous tomato plant has a Rin gene as a heterozygote together with genes giving a very firm fruit with excellent tomato-like taste which, when picked at Color 4 of the USDA color chart, has a shelf life of at least two weeks and develops a full red color. Hybrids BR-201 and BR-214 are specific examples of such plants.

9 Claims, 2 Drawing Sheets 4,843,186

LONG SHELF LIFE HETEROZYGOUS TOMATO PLANT

FIELD OF THE INVENTION

The present invention relates to new and distinct hybrids of tomato plant and more particularly to such hybrids which produce a fruit having a long shelf life while retaining its taste and firmness during the entire storage period, and developing a bright red color.

BACKGROUND OF THE INVENTION

It is an important characteristic of a tomato to have as long a storage period or shelf life as possible to allow as much time as possible for shipment and merchandising. In the past, however, tomatoes developed for long shelf life did not retain excellent tomato-like taste and firmness during the entire storage period and many did not develop a full red color. An example of such a prior art tomato claimed to have long shelf life properties is Burpee's Long Keeper. This variety does not develop a full red color nor does it maintain excellent tomato-like taste during the storage period.

SUMMARY OF THE INVENTION

Accordingly, it is an object of the present invention to produce a tomato variety which has a storage life of at least two weeks, which maintains excellent tomato-like taste and firmness throughout the entire storage period and develops a full red color.

BRIEF DESCRIPTION OF THE DRAWINGS

In the accompanying drawings.

DETAILED DESCRIPTION OF THE INVENTION

Figure 1A:
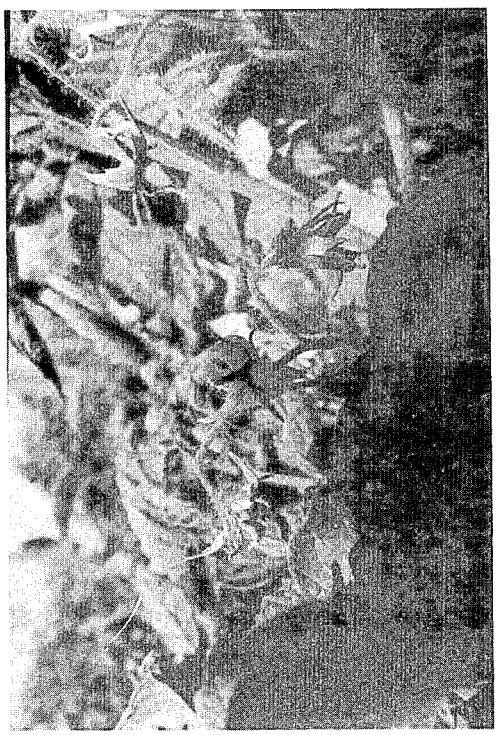
FIGS. 1A-D show typical specimens of the fruit and vegetative growth of tomato hybrid BR-201 in different stages of development, with FIG. 1B illustrating fruit specimens in cross-section.
Figure 1B:
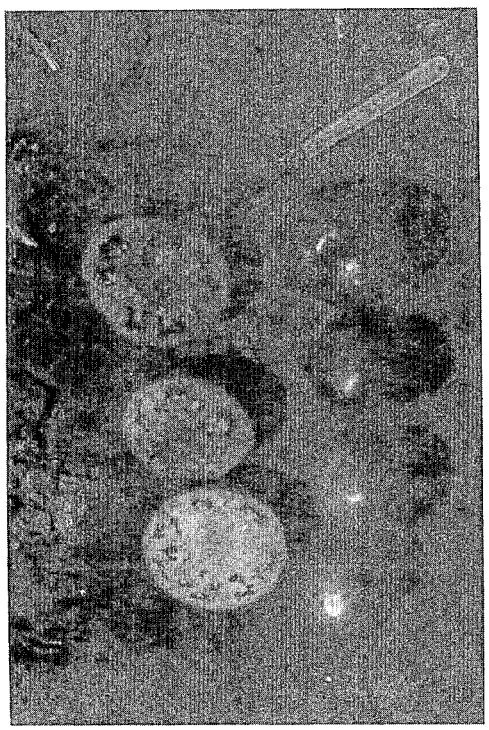
Figure 1C:
Figure 1D:
Figure 2A:
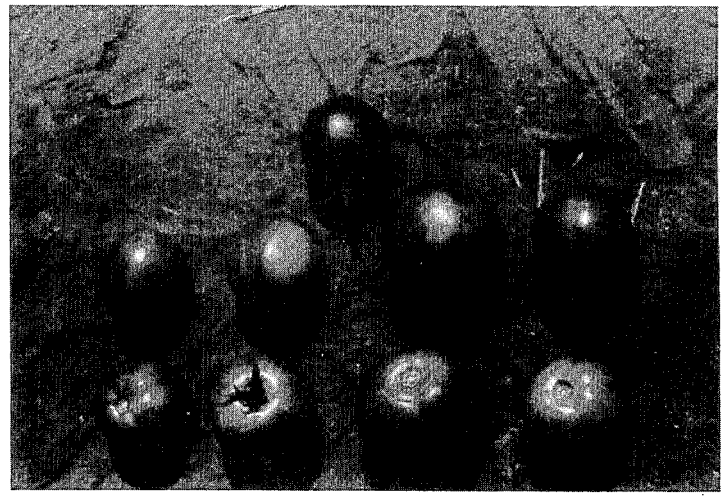
FIGS. 2A-2C show typical specimens of the fruit and vegetative growth of tomato hybrid BR-214 in different stages of development.
Figure 2B:
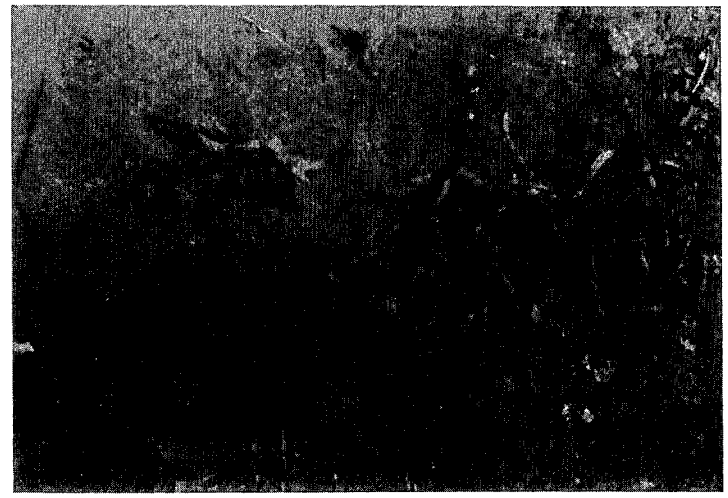
Figure 2C:
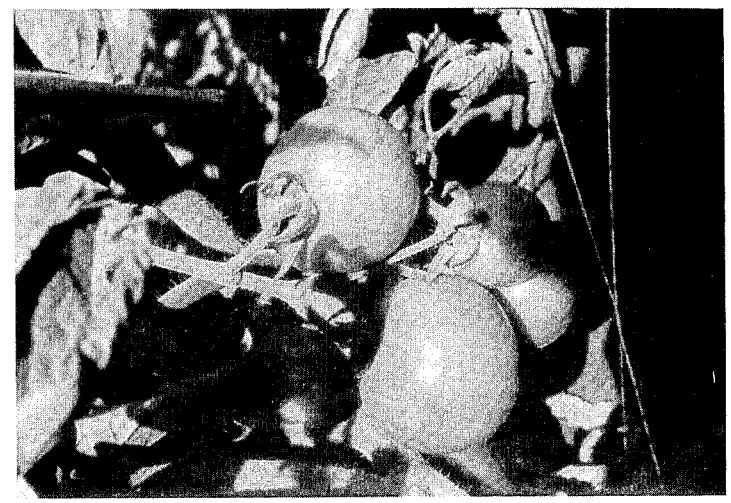

The present invention resides in a heterozygous tomato plant having a combination of genes that permit long shelf life (slow ripening) yet still allow a tomato fruit which remains firm and develops a full red color over a long storage period. The novel characteristics of the heterozygous tomato plants in accordance with the present invention include a Rin gene on one of the alleles in combination with gene which permits firmness and full ripening to a red color. Homozygous Rin/Rin tomato plants do not ripen. However, hybrids of a male parent containing the Rin/Rin gene, with a female parent, developed for the quality of not losing its taste and firmness under prolonged storage have the characteristics of the present invention. When picked at an orange to red color, designated as Color 4 according to the U.S. Department of Agriculture tomato color chart, the fruit will maintain a shelf life of at least two weeks after picking with the excellent tomato-like taste and firmness being maintained during this two week storage period. It is preferred that one or both of the parents also have the gene or series of genes which are sometimes referred to as the Israeli Firmness Factor.

The picking of fruits in accordance with the present invention at the well developed stage of Color 4 enhances the taste of the fruit which has already been bred for its excellent tomato-like taste (in its female parent). Thus, a substantial novelty of the heterozygous tomato plant in accordance with the present invention is the excellent taste of the tomato fruit, uncharacteristic to varieties containing the Rin gene which have to date been known to suffer from deteriorated taste. A further novelty for this variety is the full red color which it develops in comparison with other long shelf life varieties such as Burpee's Long Keeper.

Two hybrids which have the characteristics of the present invention have been bred and have been given the names Hybrid BR-201 and Hybrid BR-214. Seeds of these hybrids have been deposited at the American Type Culture Collection, Rockville, Maryland, on June 7, 1988, and have received the depository numbers ATCC 40460 and ATCC 40461, respectively.

Hybrid BR-201 is bred from Variety 888 as its male parent and Variety 882 as its female parent. An application for protection of Variety 888 under the Plant Variety Protection Act has been filed with the Department of Agriculture, Plant Variety Protection Office on even date herewith and has been assigned Tomato Application No. 8600143, "#888". As set forth in that PVP application, information and characteristics of Variety 888 is a homozygous Rin/Rin variety.

It is a semideterminate vigorous plant with medium to large non-ripening fruit homozygous for alcohol dehydrogenase isozyme, "fast" allele. Variety 882 is a semideterminate medium to large fruited variety homozygous for ADH (alcohol dehydrogenase) isozyme, "slow" allele. It was developed from the Valerie variety and selected for size and small blossom-end scar.

Hybrid BR-214 was bred from Variety 887 as the male parent and Variety 881 as its female parent. Variety 887 has been filed as a plant variety protection application at the Plant Variety Protection Office on even date herewith and has been assigned Tomato application No. 8600142, "#887". It is a homozygous Rin/Rin variety. It is a semi-determinate vigorous plant with medium to large nonripening fruit, homozygous for ADH isozyme and is a "fast" allele. Variety 887 is similar to 888 but is better adapted to moderate temperature and humidity conditions. Variety 881 is similar to Variety 882 but has better yield in declining temperature conditions (autumn crop with higher humidity).

While two specific hybrids are specifically described in the present application, it should be understood that the present invention is more broadly drawn to any heterozygous plant having a Rin gene as a heterozygote and having the characteristics of excellent firmness and tomato-like taste developing to a full red color during a two-week storage period, after being picked at USDA Color 4. For example, varieties other than Variety 881 and 882 can be used as the breeding partner of the Rin/Rin variety. Those of ordinary skill in the art reading the present specification will know of appropriate partners to arrive at the characteristics presently claimed. Those varieties which are known to have the characteristic known in the art as Israeli Firmness Factor are particularly suitable as one or both of said partners. It would not take undue experimentation to cross other Rin/Rin varieties with known or bred varieties known to produce tomatoes which are firm and tasty throughout their ripening period (particularly those with Israeli Firmness Factor) in order to duplicate the present invention. Such hybrids are intended to be covered by the present invention. Two other female breeding partners for Varieties 887 and 888 are Varieties 878 and 880, both of which will be the subject of Plant Variety Protection applications within a few months of the filing of the present application. Any combination of Varieties 887 or 888 with Varieties 878, 880, 881 or 882 will produce tomatoes having the characteristics in accordance with the present invention. Other combinations can also be arrived at by those skilled in the art without undue experimentation.

A detailed description of the present hybrids based on observations made from plants and fruit grown in California and Israel is as follows. Unless specified, the characteristics are the same for both hybrids.

The novel Hybrids BR-201 and BR-214 are determinate varieties, with relatively pronounced branching. They are later to harvest by approximately two weeks than Jackpot Early bush and other commercial varieties which they resemble. The fruit is almost spherical, smooth and has a slight waxy sheen. The shoulders are uniform and the blossom and scar very small. The calyx leaves curl upward and outside from the fruit. The fruit is outstandingly firm.

Hybrid BR-201 is different from Hybrid BR-214 in slightly higher growth, much less pronounced leaf roll, and slightly flatter fruit. It also is better adapted for early summer growing, whereas BR-214 is better for late summer and autumn growing.

With respect to the seedling, anthocyanin is present in the 2-5 cm seedling, and the habit of a 3-4 week seedling is normal, as opposed to compact. The mature plant at maximum vegetative development stands about 125 cm high, is of determinate growth and normal form. The canopy size is medium and its habit is semi-erect.

The stem branching is intermediate as the "Westover" variety and branching at the cotyledonary or first leafy node is absent. There are about 4-7 nodes before the first influorescence. Pubescence on younger stems is sparsely hairy.

The mature leaf beneath the third inflorescence of Hybrid BR-201 is of the normal tomato type with shallowly toothed or scalloped margins in the major leaflets and slight marginal rolling or wiltiness, with an onset in the early season. The surface of the major leaflets is rugose and the pubescence is normal. In Hybrid BR-214 the leaf is of the normal tomato type but the margins of the major leaflets are nearly entire and the marginal rolling or wiltiness is moderate, with an onset in the early season. The surface of the major leaflets is smooth and the pubescence is normal.

Observations made on the third infloresence shows the inflorescence to be of the simple type with six or seven flowers per inflorescences on the average (six for BR-201 and seven for BR-214) and with no leafy or "running" inflorescencences although such leafy inflorescences do very rarely occur in BR-214.

The calyx of the flower is normal with awl-shaped lobes, the calyx-lobes approximately equalling the corolla. The corolla color is yellow. The flower has no pubescence and the anthers all fused into a tube. Fasciation is absent.

The fruit of both hybrids is substantially spherical but that of BR-214 is slightly flatter. The transverse section of the fruit of both hybrids is substantially round, the shape of the stem end is substantially flat rather than indented, the shape of the bottom end is substantially flat as opposed to indented nippled or tapered, and the shape of the pistil scar resembles a dot. An abscission layer is present and the point of detachment of the fruit at harvest is at the pedicel joint. The length of the pedicel from the joint to the calyx attachment is approximately 13-14 mm and the length of the mature fruit along the stem axis is approximately 64-65 mm. The diameter at the widest point is approximately 71 mm. The weight of the mature fruit is approximately 190 gms. The fruit has five or more locules, and the base color of the mature green stage of the fruit is light green. The fruit is a uniform green at the mature-green stage and is full red at its full ripe stage with a red/crimson flesh color with lighter and darker areas in the walls. The locular gel color of table-ripe fruit is red and the fruit ripens from the blossom to stem end and from the inside out. The stem scar size is medium resembling that of the Rutgers variety. The epidermis is yellow and is normal peeling with a tough texture. A core is present, although it is very small in BR-214. The pericarp is 6-9 mm.

The fruit is susceptible to blotchy ripening, catface, gold fleck and zippering, but is resistant to bursting and concentric cracking. It is also known that BR-201 is resistant to radial cracking. The plant is susceptible to curly top virus but is resistant to fusarium wilt, Race 1 and Race 2. Additionally, it is known that BR-214 is susceptible to tobacco mosaic, Race 2, and tomato yellows viruses and that BR-201 is resistant to verticillium wilt, Race 1.

These hybrids are adapted to be cultured in the field and their principal use is for fresh market sale. Adaptation has been demonstrated to the southern San Joaquin Valley and desert regions of California.

It will be obvious to those skilled in the art that various changes may be made without departing from the scope of the invention and the invention is not to be considered limited to what is shown in the drawings and described in the specification.

What is claimed is:

1. A heterozygous tomato plant resulting from crossing a male parent containing the Rin/Rin gene with a female parent, said tomato plant having a Rin gene from the male parent as a heterozygote and having the characteristics of a very firm fruit with excellent tomato-like taste having a shelf like of at least two weeks, without substantially deteriorating taste or firmness, and developing a full red color.

2. Tomato fruit produced by a plant in accordance with claim 1.

3. Tomato seeds which when grown yield a tomato plant in accordance with claim 1.

4. Tomato Hybrid BR-201.

5. Tomato fruit produced by tomato hybrid BR-201 in accordance with claim 4.

6. Tomato seeds which when grown yield tomato Hybrid BR-201 in accordance with claim 4.

7. Tomato Hybrid BR-214.

8. Tomato fruit produced by tomato Hybrid BR-214 in accordance with claim 7.

9. Tomato seeds which when grown yield tomato Hybrid BR-214 in accordance with claim 7.

* * * * *

UNITED STATES PATENT AND TRADEMARK OFFICE
CERTIFICATE OF CORRECTION

PATENT NO. : 4,843,186
DATED : June 27, 1989
INVENTOR(S) : Nahum Kedar

It is certified that error appears in the above-indentified patent and that said Letters Patent is hereby corrected as shown below:

Title Page, inventor, (both printed patent and reexamination certificate), change "Nahum" to --Kedar--;
Title Page, item 75 (both printed patent and reexamination certificate), change "Kedar Nahum" to --Nahum Kedar--.

Claim 1, column 4, line 47, change "shelf like" to --shelf life--.

Signed and Sealed this

Eleventh Day of January, 2000

Attest:

Q. TODD DICKINSON

Attesting Officer

Acting Commissioner of Patents and Trademarks

US004843186B1

REEXAMINATION CERTIFICATE (3135th)

United States Patent [19]

Nahum

[11] B1 4,843,186

[45] Certificate Issued  Feb. 25, 1997

[54] LONG SHELF LIFE HETEROZYGOUS TOMATO PLANT

[75] Inventor: Kedar Nahum, Rehovot, Israel

[73] Assignee: LSL, Inc., Tiburon, Calif.

Reexamination Request:
No. 90/002,859, Oct. 7, 1992

Reexamination Certificate for:
Patent No.: 4,843,186
Issued: Jun. 27, 1989
Appl. No.: 889,915
Filed: Jul. 28, 1986

[51] Int. Cl.$^6$ .............................. A01H 1/02; A01H 5/00; A01H 5/08; A01H 5/10
[52] U.S. Cl. ................ 800/200; 800/255; 800/DIG. 44; 800/DIG. 71; 47/58; 47/DIG. 1
[58] Field of Search ................................ 800/200, 250, 800/DIG. 44; 47/58.01

[56] References Cited

PUBLICATIONS

Barkai–Golan, R. et al., "Induced ethylene evolution and climacteric-like respiration in Rhizopus–infected rin and nor tomato mutants", *Physiological Plant Pathology* 22:357–362 (1983).

Barkai–Golan, R. et al., "Pectolytic and cellulolytic activity in Rhizopus–infected rin and nor tomato mutants", *Mycopathologia* 81:123–127 (1983).

Kedar, N. et al., "Shelf–Life of Tomatoes: Breeding and Genetics", Abstracts vol. 1, XXIst International Horticultural Congress, 1982.

Kopeliovitch, E. et al., "Mode of Inheritance of Alcobaca, a Tomato Fruit–Ripening Mutant", *Euphytica* 30: 223–225 (1981).

Kopeliovitch, E. et al., "Effect of the Fruit–Ripening Mutant Genes rin and nor on the Flavor of Tomato Fruit", *Journal of the American Society for Horticultural Science* 107(3):361–364 (1982).

Kopeliovitch, E. et al., "Physiology of the tomato mutant alcobaca", *Physiol. Plant.* 48:307–311 (1980).

Tigchelaar, E. C. et al., "Natural and Ethephon–stimulated Ripening of F$_1$ Hybrids of the Ripening Inhibitor (rin) and Non–ripening (nor) Mutants of Tomato", *Aust. J. Plant Physiol.* 5:449–56 (1978).

Ignatova, S. I. et al., "Prospects of Use of Nor and Rin Genes in Breeding Tomato Hybrids which have a Long Storage Period", Dokiady Vsesoyuznoi Akademii, Sel'skokhozyaistvennykh Nauk Im. V.I. Lenina, No. 10, pp. 15–18 (1985).

Kopeliovitch, E. et al., "A Suggested Mode of Action for Rin and Nor Ripening Mutants of Tomato", *Plant Physiol.* 61:98 (1978).

Kedar, N., "Breeding tomatoes with long shelf life", Hassadeh Monthly Review of Settlement and Agriculture vol. 67, No. 12, Sep. 1987, p. 2484.

Strand et al. (1983) Vegetable Crops Research Report, Florida, Proc. 4th Tomato Quality Workshop, pp. 68 & 76.

Qapushner, et al, Agricultural Research Organization; The Volcani Center, Bit Dagan (Israel), pp. 153–160.

Kopeliovitch, et al (1979) Euphytica 28:99–104.

Kopeliovitch et al (1982) J. Amer. Soc. Hort. Sci. 107(3): 361–364.

Kedar, et al (1982) XXIst International Horticultural Congress, Abstracts, vol. 1.

Buescher, R. W. et al "Softening, Pectolytic Activiy, and Storage–Life of rin and nor Tomato Hybrids" *HortScience* 11(6):603–604, (1976).

Tigchelaar, E. C. "Genetic Regulation of Tomato Fruit Ripening" *HortScience* 13(5):508 (1978).

Tigchelaar, E. C. "Tomato Ripening Mutants" *HortScience* 13(5):502 (1978).

Ared, S. et al "Annual Report of Progress during the Growth Season 1981/1982".

Amit, Z. "Genetic improvement of flavor of long shelf–life tomatoes (Lycopersicon esculentum Mill.)"; MSc Thesis to the Faculty of Agriculture, The Hebrew University of Jerusalem, Apr., 1983.

Dayan, R. "The Growth of Tomatoes" Document sent from Israel Ministry of Agriculture Extension Service to Farmers (1983).

Bar, Z. "Food Tomatoes–Updating of Recommendation in view of Autumn 1983 Season" Document sent from Israel Ministry of Agriculture Extension Service to Farmers (1983).

Shor, A. "Marketing of Tomatoes in North America" *Garden, Field and Farm* (1985), pp. 49–51.

Dayan, R. et al "Tomato Varieties in the Arava and their Suitability for Export", Hasadeh, Feb. 1986, pp. 898–901.

Buescher, R. W., "Fruits from Rin and Nor Tomato Mutants" *Arkansas Farm Research* 26(3):14 (1977).

Strand, L. L. et al, "Taste Life of Rin and Nor Hybrids", Proceedings Fourth Tomato Quality Workshop. Mar. 7–10, 1983. Vegetable Crops Research Report (VEC–83–1), Vegetable Crops Dept., University of Florida pp. 68 & 76.

Anand, N. et al, "Breeding for extended shelf–life of tomato", *Proc. of Natl. Symp. on Produc. of Tomatoes and Chilis*, pp. 41–45 (1983).

LaPushner, D. et al, "Tomato fresh market fruit quality from a once over harvest of nor and rin hybrid arrays; Consideration for mechanical harvest production", Genetics and breeding of tomato: Proceedings of the Meeting of the Eucarpia Tomato Working Group, Avignon–France, 1981, pp. 153–160.

Kadar, A. A. et al, "Effect of Fruit Ripeness when Picked on Flavor and Composition in Fresh Market Tomatoes" *J. Amer. Soc. Hort. Sci.* 102(6):724–731 (1977).

Robinson, R. W. et al "Ripening inhibitor: a gene with multiple effect on ripening" *Tomato Genetics Coop. Rep.* 18:36,37 (1968).

*Primary Examiner*—Che Swyden Chereskin

[57]  ABSTRACT

A heterozygous tomato plant has a Rin gene as a heterozygote together with genes giving a very firm fruit with excellent tomato-like taste which, when picked at Color 4 of the USDA color chart, has a shelf life of at least two weeks and develops a full red color. Hybrids BR-201 and BR-214 are specific examples of such plants.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–9 is confirmed.

New claims 10–12 are added and determined to be patentable.

*10. A heterozygous tomato plant resulting from crossing a male parent containing the Rin/Rin gene with a female parent, said tomato plant having a Rin gene from the male parent as a heterozygote and having the characteristics of a very firm fruit with excellent tomato-like taste and having a shelf life, after being picked at color 4 of the USDA tomato color chart, of at least two weeks, without substantially deteriorating taste or firmness, and developing a full red color.*

*11. Tomato fruit produced by a plant in accordance with claim 10.*

*12. Tomato seeds which when grown yield a tomato plant in accordance with claim 10.*

\* \* \* \* \*